US007424889B2

(12) United States Patent
Mashak

(10) Patent No.: US 7,424,889 B2
(45) Date of Patent: Sep. 16, 2008

(54) CARBON DIOXIDE ABSORBER CANISTER ATTACHMENT

(75) Inventor: James N. Mashak, Sun Prairie, WI (US)

(73) Assignee: The General Electric Company, Schenectady, NY (US)

( * ) Notice: Subject to any disclaimer, the term of this patent is extended or adjusted under 35 U.S.C. 154(b) by 532 days.

(21) Appl. No.: 11/105,092

(22) Filed: Apr. 13, 2005

(65) Prior Publication Data

US 2006/0231092 A1    Oct. 19, 2006

(51) Int. Cl.
A62B 7/10 (2006.01)
A62B 23/02 (2006.01)
A62B 7/00 (2006.01)
A62B 9/00 (2006.01)
A61M 15/00 (2006.01)
A61M 16/00 (2006.01)

(52) U.S. Cl. .......................... 128/205.28; 128/200.11; 128/200.24; 128/202.22; 128/202.27; 128/203.12; 128/204.18; 128/205.12; 128/205.27; 292/247; 292/113; 292/5; 292/63; 292/163; 24/437; 24/438; 24/439; 24/440; 24/441

(58) Field of Classification Search ............ 128/200.11, 128/200.13, 200.24, 202.22, 202.27, 204.18, 128/205.27, 205.28, 910, 200.23; 24/437, 24/438, 439, 40, 441; 292/5, 63, 163, 219, 292/DIG. 11, 247, 113
See application file for complete search history.

(56) References Cited

U.S. PATENT DOCUMENTS 2,693,181 A * 11/1954 Hamilton ............... 128/202.26
2,952,526 A * 9/1960 Carlson et al. ............... 422/120
2,956,562 A * 10/1960 Leffler, Jr. ............... 128/202.26
3,974,631 A * 8/1976 Rhodes ........................ 56/202
5,168,868 A * 12/1992 Hicks ..................... 128/205.12

(Continued)

FOREIGN PATENT DOCUMENTS

DE         100 14 829 A1    10/2001

(Continued)

OTHER PUBLICATIONS

United States Patent and Trademark Office, PTO-08-2749, English Translation of DE 010014829 A1, Oct. 18, 2001, Rometsh, Water Trap, Especially for Respiratory Gas Monitoring Instruments, entire document.*

Primary Examiner—Justine R. Yu
Assistant Examiner—Clinton Ostrup
(74) Attorney, Agent, or Firm—Andrus, Sceales, Starke & Sawall, LLP

(57) ABSTRACT

An interface mechanism is provided that removably unites a carbon dioxide absorption canister with a patient breathing circuit on a ventilator. The interface mechanism includes a cradle that is moveably positioned between a first position and a second position, wherein in the first position, the canister is coupled to the cradle and the cradle is positioned such that the canister is in fluid communication with the breathing circuit. In the second position, the canister is removable from the cradle and the cradle extends at an angle from the patient breathing circuit. The interface mechanism advantageously provides visual indication when the canister is removed and the breathing circuit is operating as a closed loop system, without $CO_2$ filtration. The mechanism also facilitates efficient and accurate fluid connection between the carbon dioxide absorption canister and the breathing circuit.

14 Claims, 4 Drawing Sheets

U.S. PATENT DOCUMENTS

| | | | | |
|---|---|---|---|---|
| 5,524,615 | A * | 6/1996 | Power | 128/205.12 |
| 5,765,550 | A * | 6/1998 | Psaros et al. | 128/202.27 |
| 6,131,571 | A * | 10/2000 | Lampotang et al. | 128/204.21 |
| 6,619,289 | B1 * | 9/2003 | Mashak | 128/205.28 |
| 6,923,847 | B2 * | 8/2005 | Larsen et al. | 96/4 |
| 2004/0089155 | A1 * | 5/2004 | Larsen et al. | 96/4 |
| 2006/0231092 | A1 * | 10/2006 | Mashak | 128/200.23 |
| 2007/0051367 | A1 * | 3/2007 | Mashak et al. | 128/203.12 |

FOREIGN PATENT DOCUMENTS

EP     1230943     8/2002

* cited by examiner

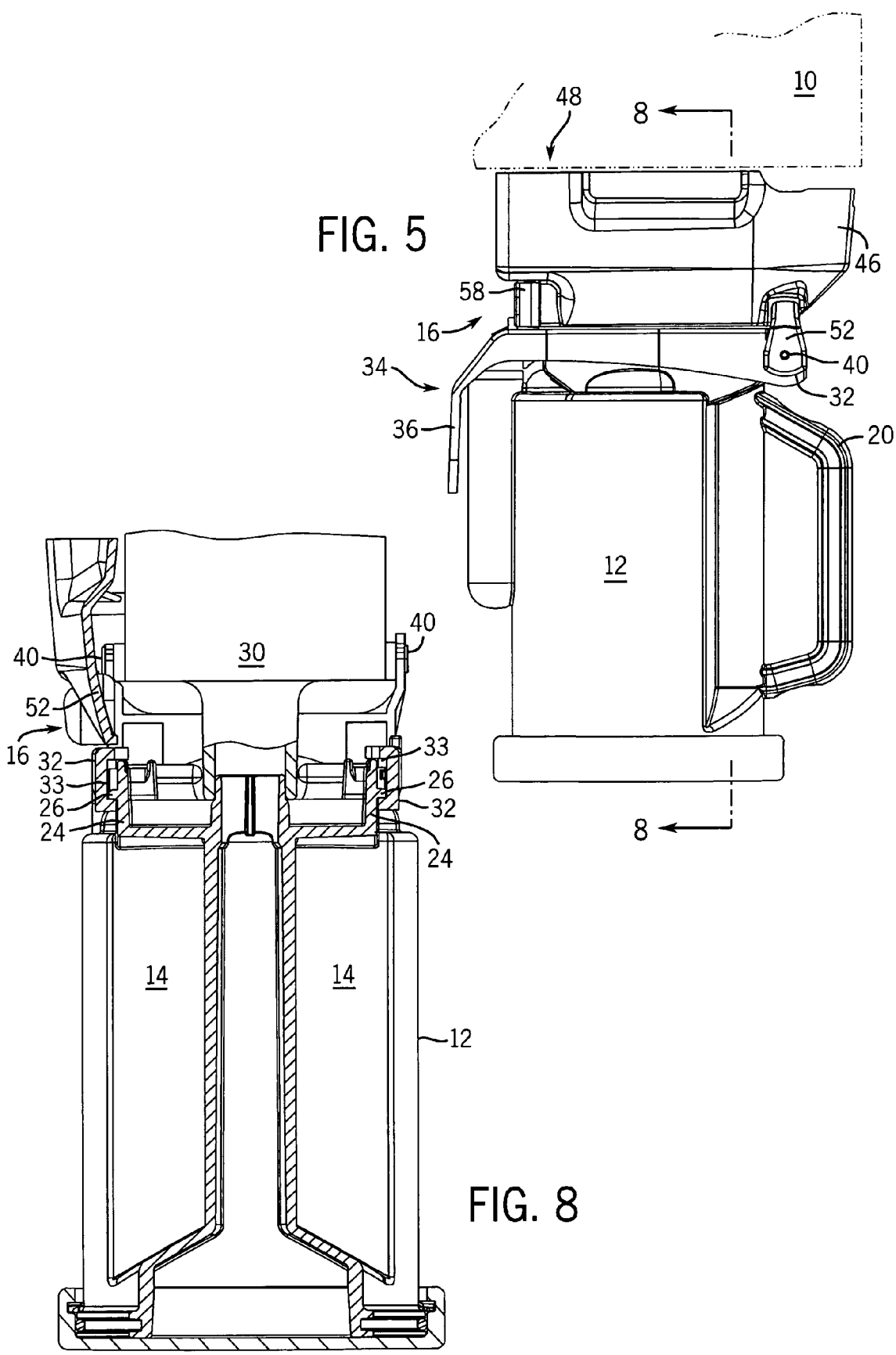

CARBON DIOXIDE ABSORBER CANISTER ATTACHMENT

BACKGROUND OF THE INVENTION

The present invention relates to anesthesia systems used to provide an anesthetic agent to a patient.

In general, anesthesia systems are utilized in medical settings and comprise various equipment to anesthetize the patient and maintain the patient in an anesthetized state until an operation or procedure is completed. Such systems typically comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient. Such limbs may be separate conduits joined by a wye piece at or near the patient or may comprise co-axial conduits commonly known as Bain circuits.

In a typical anesthesia system, the overall flow of gases to and from the patient may be in a generally closed circuit, that is, the patient is connected to a substantially closed loop supply of gases and re-breathes certain of those exhaled gases supplemented by fresh gas. Alternatively, the patient circuit could be an open circuit and all of the exhaled gases simply vented or channeled from the system to an external environment and not re-breathed by the patient. Other variety of circuits are used that deliver the anesthetic gases to the patient, such as semi-open circuits and the like.

As the driving force to the patient, a ventilator is used and which basically breathes for the patient since the patient is under anesthesia and is unable to carry out the normal spontaneous breathing functions. The ventilator, therefore, provides a quantity of gas containing a predetermined metered quantity of the anesthetic agent along with other gases such as nitrous oxide ($N_2O$) and, of course, a life sustaining percentage of oxygen.

Anesthesia systems that employ a closed circuit supply of gases typically include a canister that contains absorbent material to remove carbon dioxide ($CO_2$) from the patient gas. Periodically, the absorbent material becomes extinguished and the canister needs replacing. If the canister is replaced while the anesthesia machine is in use, two things can occur: patient circuit gas is released into the room while the canister is off, or there is no loss of patient circuit gas if the breathing system is equipped with a $CO_2$ bypass mechanism. The latter arrangement is addressed by the present invention.

When the $CO_2$ bypass mechanism is actuated by the removal of the absorbent canister, the breathing circuit functions as normal, except for the removal of $CO_2$. This is acceptable for a short period of time until a new canister is substituted. It is during $CO_2$ bypass that awareness should be maintained that the machine is operating in the bypass mode. However, distractions can occur that remove the caregiver's attention from installing a new canister. Once attention is regained, the user may fail to notice the missing canister because the system appears to be functioning normally. If the system continues to operate without the $CO_2$ bypass, serious medical complications to the patient can occur.

SUMMARY OF THE INVENTION

By the present invention, it is recognized as desirable to provide visible indication when the carbon dioxide absorption canister is detached from the breathing circuit. It is further recognized as desirable to provide means for removably connecting the canister to the breathing circuit that is easy to use and affords repeated, accurate connections.

According to one embodiment of the present invention, an interface mechanism is provided for removably uniting the carbon dioxide absorption canister with the patient breathing circuit on the ventilator. The interface mechanism includes a cradle that is moveably positionable between a first position and a second position. In the first position, the canister is attached to the cradle and the cradle is positioned such that the canister is in fluid communication with the breathing circuit to remove carbon dioxide from breathing gas within the circuit. In the second position, the canister is removable from the cradle, at which point a $CO_2$ bypass mechanism is actuated to close the breathing system. When the canister is removed, the cradle extends at an angle from the breathing circuit and provides visual indication that the canister is removed.

In a particular embodiment, the interface mechanism includes a mounting bracket connected to the breathing circuit and a cradle connected to the mounting bracket by a hinge. A latch is provided that releasably connects the cradle to the mounting bracket when the cradle is moved into the aforementioned first position. The cradle can include a pair of opposing arms sized and shaped to receive and removably retain opposing rails on the canister.

The interface mechanism visually indicates to caregivers that the canister is removed from the breathing circuit and the $CO_2$ bypass mechanism is in operation. As such, caregivers will be less likely to forget to reattach a replenished absorption canister. This feature can avoid serious medical complications to the patient. In addition, the interface mechanism is arranged such that the canister can be easily connected to and disconnected from the breathing circuit. The interface further provides a secure interlock and encourages proper attachment of the canister.

These and other advantages of the present invention will be apparent to those of skill in the art, with reference to the following drawing figures and detailed description.

BRIEF DESCRIPTION OF THE DRAWINGS

Preferred embodiments of the best mode of carrying out the invention are described with reference to the following drawing figures, wherein:

FIG. 5 is a side view of the canister attached to the interface mechanism positioned such that the canister is in fluid communication with the breathing circuit;

FIG. 8 is a sectional view taken along line 8-8 shown in FIG. 5.

DETAILED DESCRIPTION OF THE PREFERRED EMBODIMENTS

The present invention pertains to an interface mechanism for removably uniting a carbon dioxide absorption canister with a patient breathing circuit of a ventilator. It should be recognized that the following detailed description and attached figures are an exemplification of the principles of the invention, which is more particularly defined in the appended claims. The invention is not limited to the particular examples shown and described herein.

Figure 1:
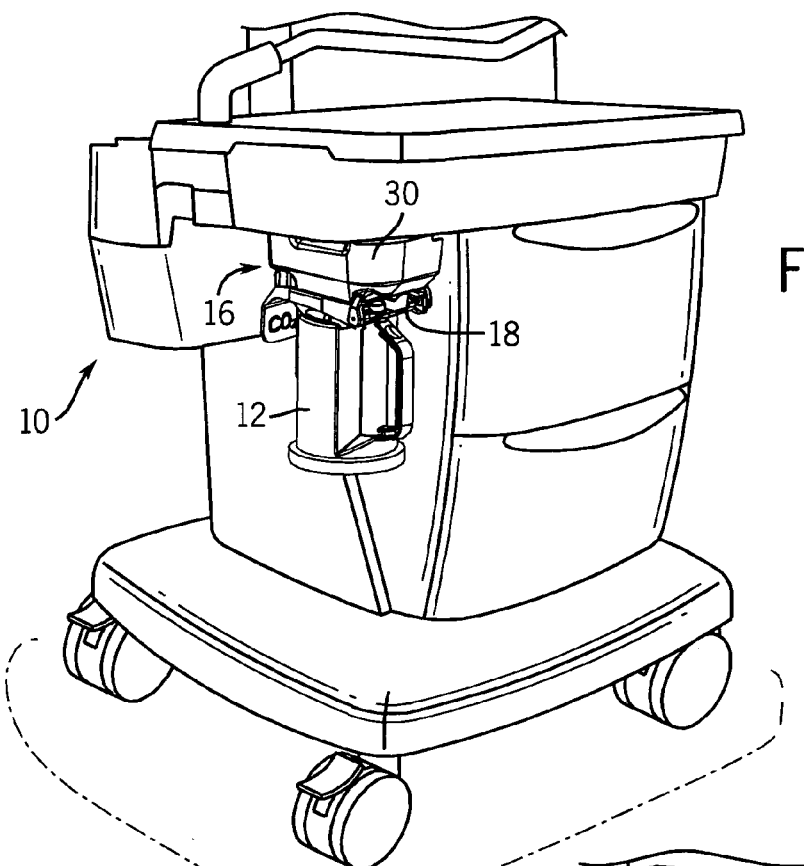
FIG. 1 is a perspective view of an anesthesia machine having a carbon dioxide absorber canister attached thereto.

Referring to FIG. 1, an anesthesia system incorporating a ventilator 10 is shown in perspective view. The overall flow of gases to and from the ventilator 10 is a generally closed circuit, that is, the patient is connected to a substantially closed loop supply of gases and re-breathes certain of those exhaled gases supplemented by fresh gas. The ventilator 10, therefore, provides a quantity of gas containing a predetermined metered quantity of anesthetic agent along with other gases such as $N_2O$ and, of course, a life-sustaining percentage of oxygen. A carbon dioxide absorber canister 12 is attached to the closed circuit supply of gases to remove carbon dioxide from the patient gas. The absorber canister 12 contains absorbent material 14 (see FIG. 8) which absorbs the carbon dioxide in the patient gas. Periodically, the absorbent material 14 becomes extinguished and the absorber canister 12 needs replacing. The ventilator 10 is of the type having a carbon dioxide bypass mechanism (not shown) that is actuated by removal of the absorber canister 12 from the patient circuit. When the carbon dioxide bypass mechanism is actuated, the breathing circuit functions as normal, except for the removal of carbon dioxide. In other words, there is no loss of patient circuit gas when the carbon dioxide absorber canister 12 is removed and the bypass mechanism is actuated. This is acceptable for a short period of time until a new canister is substituted, however it is unacceptable for longer periods of time because the amount of carbon dioxide in the closed circuit can rise to unacceptable and even life-threatening levels.

Figure 1A:
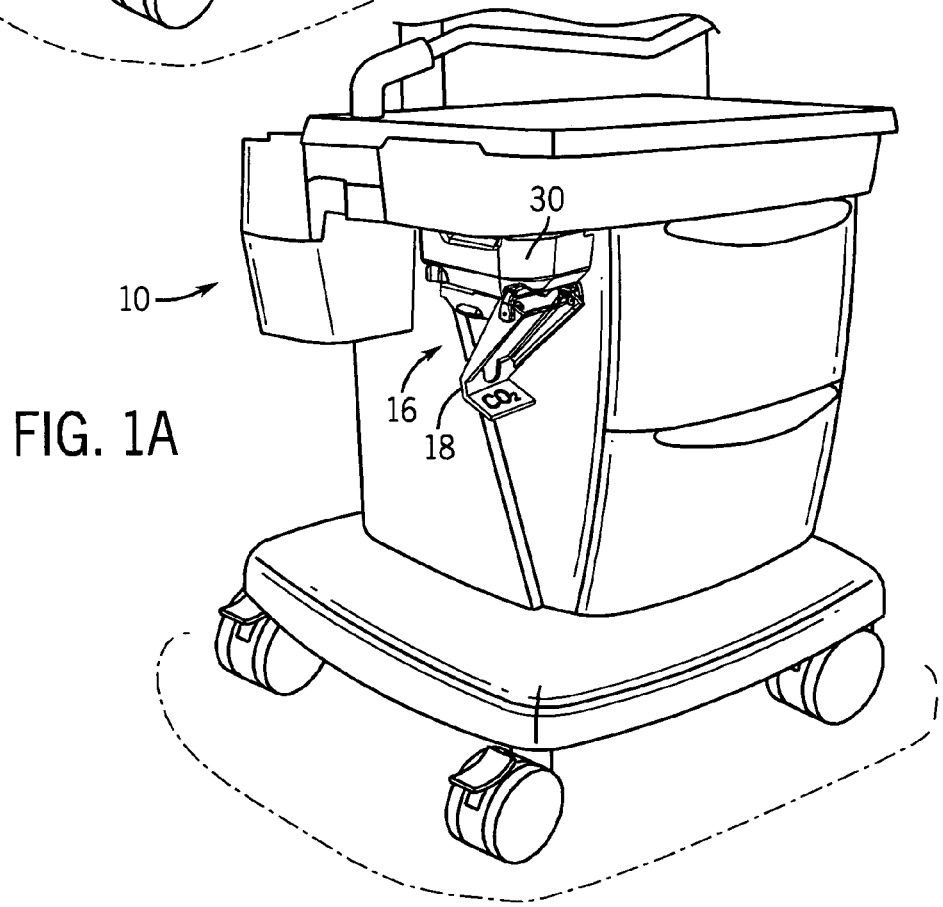
FIG. 1A is the anesthesia machine shown in FIG. 1, wherein the carbon dioxide absorber canister is detached.

Referring the FIGS. 1 and 1A, an interface mechanism 16 is provided for removably uniting the carbon dioxide absorption canister 12 with the breathing circuit on the ventilator 10. The interface mechanism 16 includes, generally, a cradle 18 that is movably positionable between a first position (FIG. 1) wherein the canister 12 is attached to the cradle 18 and the cradle 18 is positioned such that the canister 12 is in fluid communication with the breathing circuit to remove carbon dioxide from breathing gas within the circuit, and a second position (FIG. 1A) wherein the canister 12 is removable from the cradle 18, at which point the carbon dioxide bypass mechanism is actuated to close the breathing circuit off from atmosphere. As shown in FIG. 1A, when the canister 12 is removed, the cradle 18 extends at an angle from the breathing circuit and ventilator 10 and provides visual indication that the canister 12 is removed.

Figure 2:
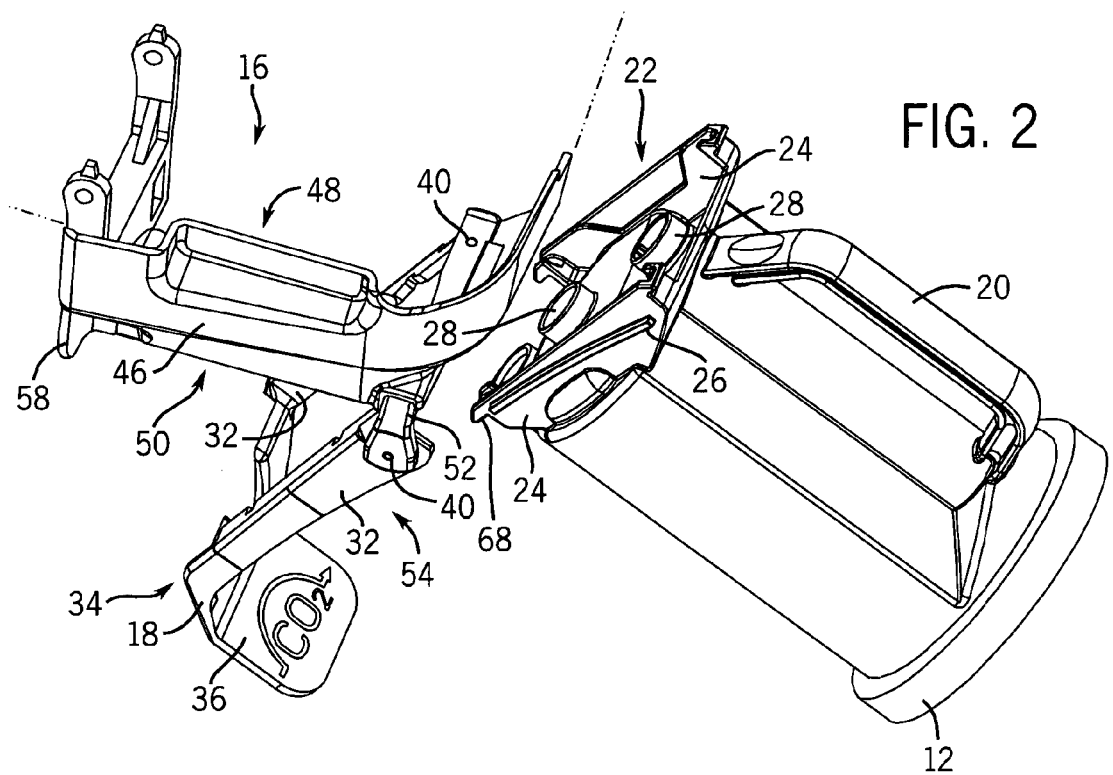
FIG. 2 is a top angled perspective view of an interface mechanism for removably uniting a carbon dioxide absorption canister with a patient breathing circuit of a ventilator.

Referring to FIG. 2, the canister 12 is generally cylindrical in shape and includes a handle 20 arranged to be manually grasped by the caregiver. The top portion 22 of the canister 12 includes a pair of opposed arms 24, each of which have an outer surface that carries an elongated transversely extending rail 26. The top portion 22 of the canister 12 further includes inlet and outlet holes 28 sized to be compatible with corresponding inlet and outlet holes on the breathing circuit or ventilator 10, which are shown as 27 in FIG. 7. It will be recognized however that the present invention can be designed to operate with other types of carbon dioxide absorber devices, rather than the particular canister 12 illustrated in the figures.

Figure 6:
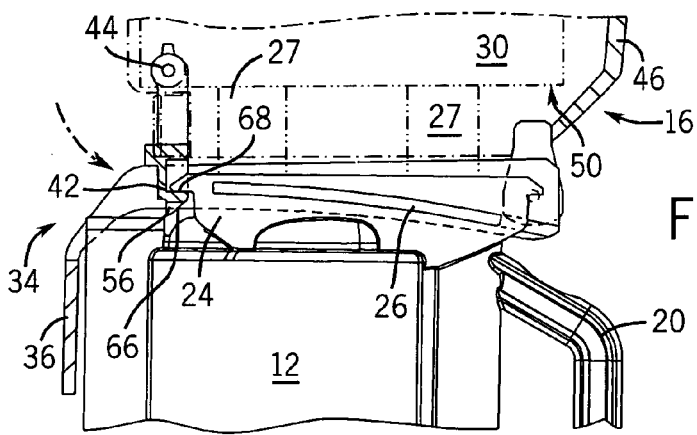
FIG. 6 is a side view of the interface mechanism showing a latch mechanism releasably coupling the canister to the breathing circuit.
Figure 7:
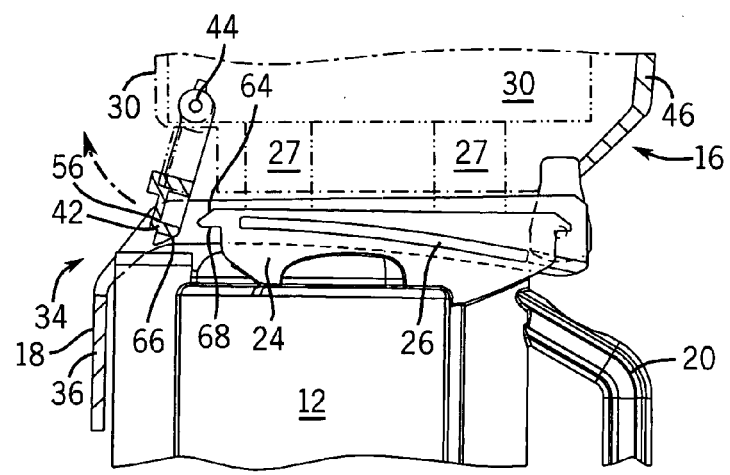
FIG. 7 is a side view of the interface mechanism showing the latch mechanism releasing the canister from the breathing circuit.

The interface mechanism 16 includes the cradle 18, which is pivotally mounted to a retainer 30 (shown illustratively in FIGS. 6 and 7). The cradle 18 includes a pair of opposing arms 32 that are sized and shaped to receive and removably retain the top portion 22 of the absorber canister 12. More specifically, the interior surface of each of the opposed arms 32 includes a channel 33 (shown most clearly in FIG. 8) shaped slightly larger than the rails 26 on the opposed arms 24 of the canister 12. The opposed arms are interconnected at a distal end 34 by a cross member 36. The cross member 36 closes the arms 32 to form a U-shape and which also functions as a sign.

The proximal ends of the opposed arms 32 of the cradle 18 are pivotally attached to the retainer 30 at pivot points 40.

Figure 3:
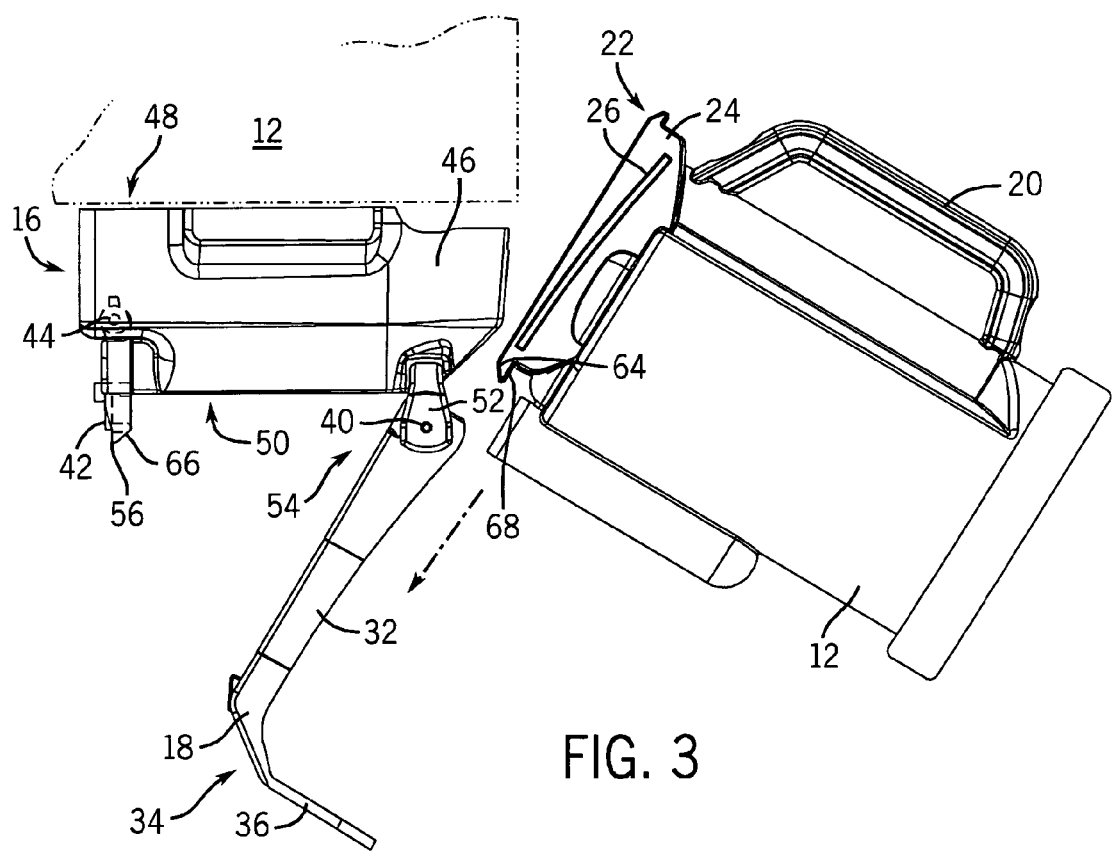
FIG. 3 is a side view of the carbon dioxide absorption canister being slid into a cradle of the interface mechanism.

Referring to FIGS. 2 and 3, the retainer 30 is arranged to be fixedly connected to the ventilator 10 and more particularly to the ventilator 10 along the closed breathing circuit. The retainer 30 includes a downwardly extending latch member 42 that is pivotable about pivot point 44. The retainer further includes a cover 46 and has an upper side 48 for attachment to the ventilator 10 and a lower side 50 for attachment to the cradle 18. Downwardly extending hinge members 52 extend from the proximal end 54 of the lower side 50 of the retainer 30. The downwardly extending hinge members 52 hingedly connect to the pivot points 40 on the cradle 18.

Referring to FIG. 3, the latch member 42 of the retainer 30 comprises an L-shaped member 56 that is pivotable about pivot point 44. The latch member further includes an outwardly extending tab 58 (FIG. 2) that can be manually actuated by the caregiver to pivot the L-shaped member 56 about the pivot point 44 in a clockwise direction, as shown in FIG. 7.

Figure 4:
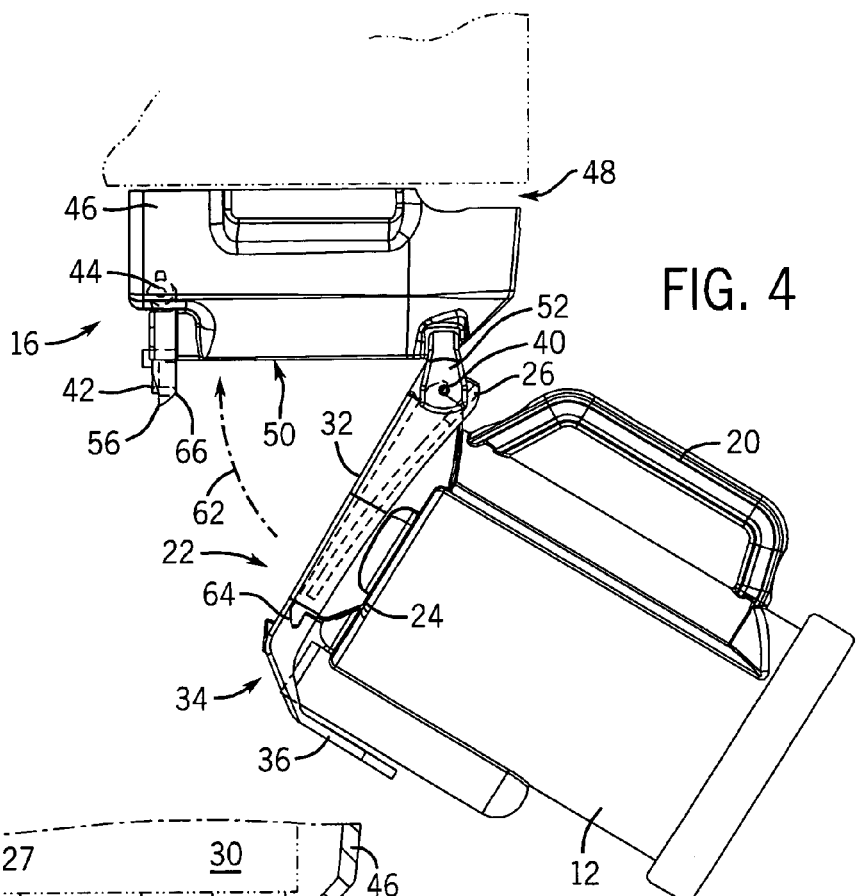
FIG. 4 is a side view of the cradle of FIG. 3 moving from a second position to a first position.

As shown in FIG. 3, the canister 12 is inserted onto the cradle 18 by sliding the top portion 22 of the canister 12 between the opposed arms 32 such that the rails 26 engage the channels 33 on the inside portion of the opposed arms 32. Insertion of the canister 12 is complete once the canister 12 is fully seated in the opposed arms, as shown in FIG. 4. Referring to FIG. 4, the canister 12 is connected to the ventilator 10, and the breathing circuit, by pivoting the cradle 18 in the clockwise direction, as shown in FIG. 4, along arrow 62.

As shown in FIGS. 4 and 6, the opposed arms 24 of the canister 12 include a sloped surface 64. The latch members 42 also include a rearward sloped surface 66 sized and shaped to engage the sloped surface 64 of the opposed arms 24 when the cradle 18 is pivoted into a first position, shown in FIG. 6. When the forward sloped surface 64 engages the rearward sloped surface 66, the latch member 42 is biased about the pivot point 44 and the forward sloped surface 64 passes by the rearward sloped surface 66. Once the forward sloped surface 64 is completely past the rearward sloped surface 66, the latch member 42 biases into a closed position, shown in FIG. 6. The latch members 42 may be normally biased into the closed position by, for example, a coil spring (not shown). The L-shaped member 56 thus engages a base surface 68 on the opposed arms 24, to retain the cradle in the first position, coupled to the retainer 30.

As shown in FIG. 7, when the cradle 18 is pivoted into the first position, the inlet and outlet holes 28 are mated with corresponding inlet and outlet holes 27 on the ventilator 10, thus uniting the canister with the breathing circuit on the ventilator 10 and providing fluid communication therebetween.

When it is desired to remove the canister 12 from engagement with the ventilator 10, the caregiver manually actuates tab 58 to pivot the latch member 42 in the clockwise direction, as shown in FIG. 7. The L-shaped member 56 thus disengages the base surface 68 on the opposed arms 24, freeing the cradle 18. Gravity causes the cradle 18 to pivot about pivot points 40 into the second position, shown in FIG. 1A. The canister 12 may thus be removed from the cradle 18 by sliding the top portion 22 of the canister 12 in a direction opposite that shown in FIG. 3.

It will thus be seen that the interface mechanism provides a unique arrangement that removably unites a carbon dioxide absorption canister with a patient breathing circuit on a ventilator. The interface mechanism advantageously provides visual indication when the canister is removed and the breathing circuit is operating as a closed loop system, without carbon dioxide filtration. The mechanism facilitates efficient and accurate fluid connection between the carbon dioxide absorption canister and the breathing circuit.

What is claimed is:

1. An arrangement for connecting a carbon dioxide adsorption canister to a patient breathing circuit of a ventilator, the arrangement comprising:
   a ventilator having a patient breathing circuit;
   a carbon dioxide adsorption canister; and
   an interface mechanism removably coupled to the ventilator and configured to removably connect the carbon dioxide absorption canister to the patient breathing circuit, the interface mechanism having
      a retainer that is connected to the ventilator and that has a passageway connected to the patient breathing circuit;
      a cradle that is coupled to the retainer and that is configured to receive and removably retain the carbon dioxide adsorption canister, the cradle being positionable between first and second positions relative to the retainer while remaining coupled to the retainer;
   wherein in the first position, the cradle is horizontally aligned with the retainer and in the second position the cradle is not horizontally aligned with the retainer;
   wherein the canister and the retainer have mating faces that mate together when the cradle is positioned in the first position;
   wherein in the first position the canister is coupled to the cradle and the mating faces are mated, and the canister is placed in fluid communication with the patient breathing circuit via the passageway of the retainer; and
   wherein in the second position the mating faces are not mated, the canister is not connected to the patient breathing circuit, and the cradle extends at an angle from the retainer and thereby provides visual indication when the canister is removed from the interface mechanism.

2. The arrangement of claim 1, comprising a hinge that attaches the cradle to the retainer and wherein the cradle is pivotable between the first and second positions about the hinge.

3. The arrangement of claim 1, comprising a latch mechanism that releasably couples the cradle into the first position.

4. The arrangement of claim 3, wherein the latch mechanism is part of the retainer.

5. The arrangement of claim 3, wherein the latch mechanism comprises an L-shaped member that engages a portion of the canister when the cradle is in the first position.

6. The arrangement of claim 5, wherein the latch mechanism comprises a tab and wherein the tab is manually actuatable to move the L-shaped member and thereby release the cradle from the first position.

7. The arrangement of claim 1, wherein the cradle comprises a pair of opposing arms.

8. The arrangement of claim 7, wherein the pair of opposing arms are each attached to the retainer by a hinge.

9. The arrangement of claim 7, wherein the pair of opposing arms are joined by a cross member.

10. The arrangement of claim 9, wherein the cross member comprises a sign.

11. The arrangement of claim 7, wherein the canister comprises a pair of opposing arms that engage the pair of opposing arms on the cradle to connect the canister to the cradle.

12. The arrangement of claim 11, wherein the respective opposing arms of the cradle and canister are engaged by a slot-and-groove connection.

13. The arrangement of claim 1, wherein the breathing circuit comprises a closed-loop system.

14. The arrangement of claim 1, wherein the passageway of the retainer comprises a pair of holes, and wherein the canister comprises a pair of holes that mate with the pair of holes on the retainer when the cradle is in the first position.

\* \* \* \* \*